(12) United States Patent
Centanni et al.

(10) Patent No.: US 7,232,545 B2
(45) Date of Patent: Jun. 19, 2007

(54) SENSOR FOR DETERMINING CONCENTRATION OF FLUID STERILANT

(75) Inventors: Michael A. Centanni, Parma, OH (US); Chung-Chiun Liu, Cleveland Heights, OH (US); Dong Zhao, Cleveland, OH (US); Jinsong Yu, Cleveland Heights, OH (US)

(73) Assignee: Steris Inc., Temecula, CA (US)

( * ) Notice: Subject to any disclaimer, the term of this patent is extended or adjusted under 35 U.S.C. 154(b) by 224 days.

(21) Appl. No.: 10/663,593

(22) Filed: Sep. 16, 2003

(65) Prior Publication Data
US 2005/0063882 A1 Mar. 24, 2005

(51) Int. Cl.
*G01N 29/02* (2006.01)

(52) U.S. Cl. .............. 422/3; 422/88; 436/135; 73/24.06; 73/31.05

(58) Field of Classification Search .............. 422/88, 422/3, 4; 436/135; 73/24.06, 31.05; 324/464
See application file for complete search history.

(56) References Cited

U.S. PATENT DOCUMENTS

| | | | |
|---|---|---|---|
| 3,164,004 A | 1/1965 | King, Jr. ............... 73/24.06 |
| 3,327,519 A | 6/1967 | Crawford ............... 73/24.06 |
| 3,464,797 A | 9/1969 | Hagopain ............... 23/232 |
| 4,111,036 A * | 9/1978 | Frechette et al. ......... 73/24.06 |
| 4,163,384 A | 8/1979 | Blakemore ................ 73/29 |
| 4,236,893 A | 12/1980 | Rice ..................... 23/230 B |
| 4,242,096 A | 12/1980 | Oliveira et al. ......... 23/230 B |
| 4,314,821 A | 2/1982 | Rice .................... 23/230 B |
| 4,788,466 A | 11/1988 | Paul et al. ............... 310/316 |
| 4,849,178 A | 7/1989 | Azuma .................... 422/69 |
| 5,339,675 A | 8/1994 | DiLeo et al. ............ 43/24.04 |
| 5,595,908 A | 1/1997 | Fawcett et al. ......... 435/287.2 |
| 5,700,375 A | 12/1997 | Hagen et al. ............ 210/651 |
| 5,705,399 A * | 1/1998 | Larue .................... 436/501 |
| 5,756,631 A | 5/1998 | Grate ..................... 528/26 |
| 5,856,198 A | 1/1999 | Joffe et al. .............. 436/100 |
| 5,866,798 A | 2/1999 | Schönfeld et al. ........ 73/24.06 |
| 5,958,787 A * | 9/1999 | Schonfeld et al. ........ 436/116 |
| 6,077,480 A * | 6/2000 | Edwards et al. ........... 422/28 |
| 6,171,867 B1 | 1/2001 | Feucht et al. ............ 436/124 |
| 6,196,052 B1* | 3/2001 | May et al. .............. 73/24.06 |
| 6,410,332 B1 | 6/2002 | Desrosiers et al. ........ 436/37 |
| 6,560,551 B1 | 5/2003 | Severson et al. .......... 702/54 |
| 6,630,560 B2 | 10/2003 | McGill et al. ............ 528/25 |
| 2003/0132279 A1* | 7/2003 | Stemmie .................. 232/31 |

OTHER PUBLICATIONS

Ishihara, Tatsumi et al. "Mixed oxide capacitor of barium titanate-lead oxide as a new type of carbon dioxide gas sensor," Chemistry Letters (1990), (7), pp. 1163-1166.*

Taguchi, Masami et al. "Analysis of discharge/charge reaction of PbO2 thin film electrode by using electrochemical QCM technique", Nippon Kinzoku Gakkaishi (2002), 66(6), pp. 670-675.*

(Continued)

*Primary Examiner*—E. Leigh McKane
(74) *Attorney, Agent, or Firm*—Kusner & Jaffe; Michael A. Centanni (57) ABSTRACT

A sensor for detecting hydrogen peroxide, comprising an element exhibiting piezoelectric properties having a metal-oxide-containing coating, the metal-oxide having a divalent or tetravalent state.

7 Claims, 4 Drawing Sheets

OTHER PUBLICATIONS

Steven J. Lasky, Howard R. Meyer & Daniel A. Buttry, Department of Chemistry, "Quartz Microbalance Studies of Solvent and Ion Transport in Thin Polymer Films in Sensor Applications of the QCH," *Technical Digest* 1990, pp. 1-4.

Sylvain Lazare and Vincent Granier, "Excimer Laser Light Induced Ablation and Reactions at Polymer Surfaces as Measured with a Quartz-Crystal Microbalance," Nov. 16, 1987, J. Appl. Phys 63 (6), Mar. 15, 1988, 1988 *American Institute of Physics*, pp. 2110-2115.

Stanley Bruckenstein, C. Paul Wilde, Michael Shay and A. Robert Hillman, "Experimental Observations on Transport Phenomena Accompanying Redox Switching in Polythionine Films Immersed in Strong Acid Solutions," 1990 American Chemical Society, pp. 787-793.

Robert R. McCaffrey, Stanley Bruckenstein and Paras N. Prasad, "Novel Application of the Quartz Crystal Microbalance to Study Langmuir-Blodgett Films," 1986 *American Chemical Society*, pp. 228-229.

J.A. Moore and Sang Youl Kim, "Diffusion of Small Molecules in Radiation Damaged PMMA Thin Films," 2002 Engineering Info. Inc., pp. 383-386.

Rade Ognjanovic, C.-Y. Hui, E.J. Kramer, "The Study of Polystyrene Surface Swelling by Quartz Crystal Microbalance and Rutherford Backscattering Techniques," *Journal of Materials Science* 25 (1990), 1990 Chapman and Hall Ltd., pp. 514-518.

H.G. Tompkins, "Use of Surface and Thin Film Analysis Techniques to Study Metal-Organic and Metal-Polymer Interaction: A Review," *Thin Solid Films*, 119 (1984), pp. 337-348.

Sylvain Lazare, Jean Claude Soulignac and Pascal Fragnaud, "Direct and Accurate Measurement of Etch Rate of Polymer Films under Far-UV Irradiation," Appl. Phys. Lett. 50 (10), Mar. 9, 1987, 1987 American Institute of Physics, pp. 624-625.

Aljosa Vrhunec, Andreja Kolenc, Dusan Teslic, Iztok Livk and Ciril Pohar, "Crystal Size Distribution in Batch Sodium Perborate Precipitation," *Acta Chim. Slov.* 1999, 46(4), pp. 543-554.

U.S. Appl. No. 10/987,072, filed Nov. 12, 2004, Centanni, entitled: Sensor for Determining Concentration of Ozone.

* cited by examiner

SENSOR FOR DETERMINING CONCENTRATION OF FLUID STERILANT

FIELD OF THE INVENTION

The present invention relates generally to decontamination systems, and more particularly to a sensor for determining the concentration of a decontaminant.

BACKGROUND OF THE INVENTION

Sterilization and decontamination methods are used in a broad range of applications, and have used an equally broad range of sterilization agents. As used herein the term "sterilization" refers to the inactivation of all bio-contamination, especially on inanimate objects. The term "disinfectant" refers to the inactivation of organisms considered pathogenic.

Sterilization/decontamination systems rely on maintaining certain process parameters in order to achieve a target sterility or decontamination assurance level. For hydrogen peroxide vapor sterilization/decontamination systems, those parameters include the concentration of the hydrogen peroxide vapor, the degree of saturation, the temperature and pressure and the exposure time. By controlling these parameters, the desired sterility assurance levels can be successfully obtained while avoiding condensation of the hydrogen peroxide due to vapor saturation.

Because of the potential for degradation of the sterilant, monitoring the hydrogen peroxide concentration within a sterilization or decontamination chamber is important to ascertain whether sufficient sterilant concentration is maintained long enough to effect sterilization of objects within the chamber. In this respect, it is desirable that measurements of the concentration of a sterilant or decontaminant be made in real time as a sterilization process proceeds.

The present invention provides a sensor for detecting the concentrations of a sterilant or decontaminant.

SUMMARY OF THE INVENTION

In accordance with a preferred embodiment of the present invention, there is provided a sensor for detecting hydrogen peroxide, comprising an element exhibiting piezoelectric properties having a metal-oxide-containing coating, the metal-oxide having a divalent or tetravalent state.

In accordance with another aspect of the present invention, there is provided a sensor for detecting hydrogen peroxide, comprising a substrate exhibiting piezoelectric properties having first and second major surfaces. A first electrode is connected to the first major surface and a second electrode connected to the second major surface. A layer of a material is provided on at least one of the first and second major surfaces. The material is operable to change the mass of the sensor when exposed to hydrogen peroxide.

In accordance with another aspect of the present invention, there is provided a method of determining the presence of a sterilant in a region of a decontamination system having a chamber defining the region and a circulation system for supplying the sterilant to the region, comprising the steps of:

providing in the region an element having piezoelectric properties with a metal oxide coating having a divalent or tetravalent state;

determining a baseline frequency of oscillation for the element in the absence of the sterilant;

determining a sensed frequency of oscillation for the element when exposed to the sterilant in the region; and determining the concentration of the sterilant in the region based upon the difference between the sensed frequency and the baseline frequency.

In accordance with yet another aspect of the present invention, there is provided a system for the deactivation of bio-contamination, comprising a system for moving a sterilant through a space. A piezoelectric device that supports a material that interacts with the sterilant is disposed in the space. The piezoelectric device has a frequency that changes in response to the presence of the sterilant. A controller is provided having data stored therein relating to the piezoelectric device. The data relate a frequency of the piezoelectric device to a concentration of the sterilant.

An advantage of the present invention is a sensor for determining the concentration of a sterilant or decontaminant, such as vaporized hydrogen peroxide.

Another advantage of the present invention is a sensor as described above that can determine the concentration of a sterilant or decontaminant, such as vaporized hydrogen peroxide, during the course of a decontamination cycle.

Another advantage of the present invention is a sensor as described above that is reusable.

These and other objects will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
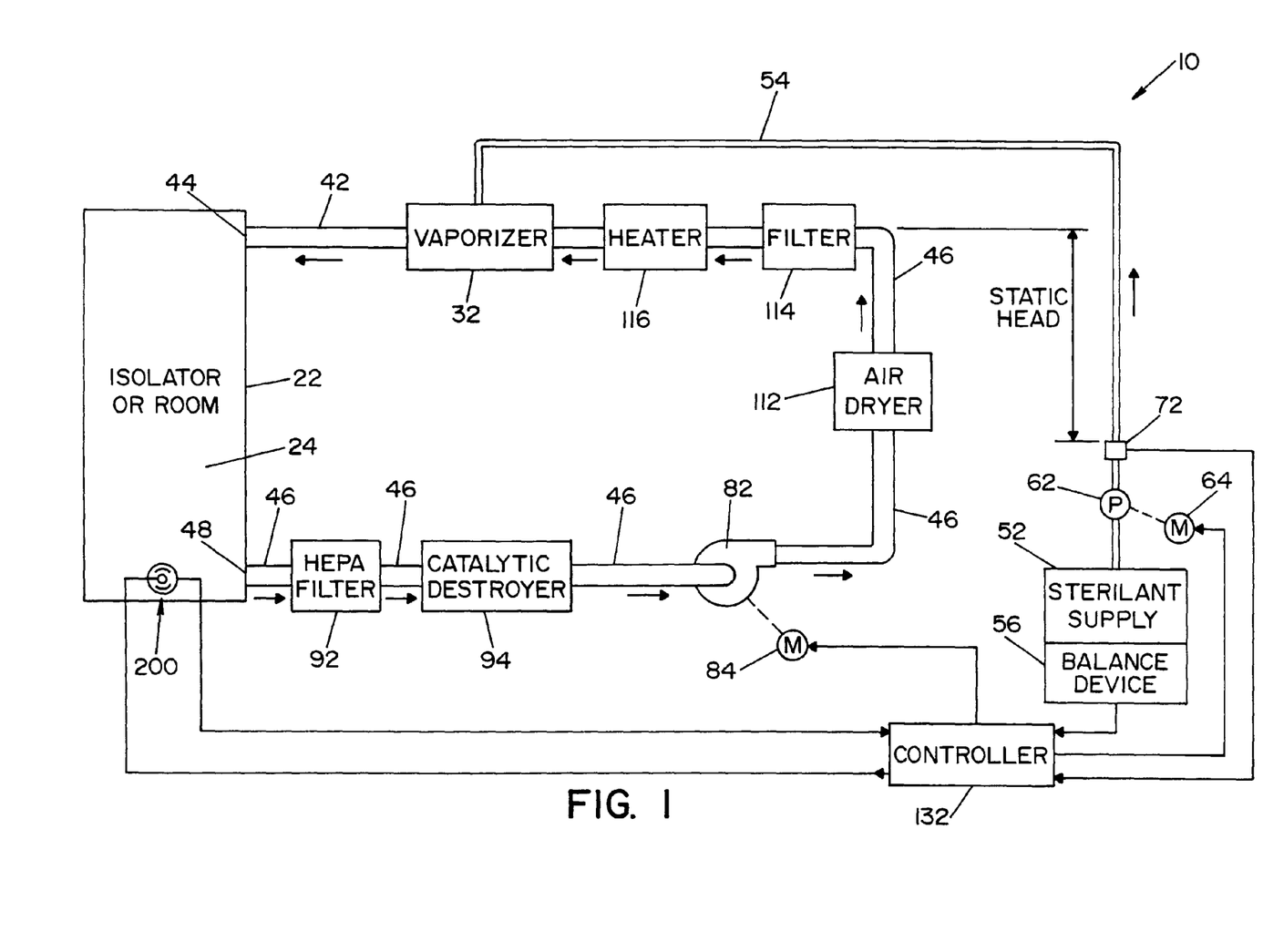
FIG. 1 is a schematic view of a decontamination system.

Referring now to the drawings wherein the showings are for the purpose of illustrating a preferred embodiment of the invention only, and not for the purpose of limiting same, FIG. 1 shows a decontamination system 10 having a sensor 200 for determining the concentration of a decontaminant or sterilant used within system 10. In the embodiment shown, system 10 is a closed-loop decontamination system for decontaminating objects with hydrogen peroxide, and more particularly, with vaporized hydrogen peroxide. Accordingly, sensor 200 shall be described with respect to determining the concentration of vaporized hydrogen peroxide in a two-component, vapor-phase sterilant. It will of course be appreciated that a sensor 200 according to the present invention may find advantageous application in determining the concentration of other fluid, i.e., other gaseous, vaporous or liquid sterilants or decontaminants.

In the embodiment shown, system 10 includes an isolator or room 22 that defines an inner sterilization/decontamination chamber or region 24. It is contemplated that articles to be sterilized or decontaminated may be disposed within isolator or room 22. A vaporizer (also referred to as generator) 32 is connected to sterilization/decontamination chamber or region 24 of room or isolator 22 by means of a supply conduit 42. Supply conduit 42 defines an inlet 44 to chamber or region 24. Vaporizer 32 is connected to a liquid sterilant supply 52 by a feed line 54. A conventionally known balance device 56 is associated with sterilant supply 52, to measure the actual mass of sterilant being supplied to vaporizer 32.

A pump 62 driven by a motor 64 is provided to convey metered amounts of the liquid sterilant to vaporizer 32 where the sterilant is vaporized by conventionally known means. In an alternate embodiment, pump 62 is provided with an encoder (not shown) that allows monitoring of the amount of sterilant being metered to vaporizer 32. If an encoder is provided with pump 62, balance device 56 is not required. A pressure switch 72 is provided in the feed line. Pressure switch 72 is operable to provide an electrical signal in the event that a certain static head pressure does not exist in feed line 54.

Isolator or room 22 and vaporizer 32 are part of a closed loop system that includes a return conduit 46 that connects an outlet port 48 to isolator or room 22 (and sterilization/decontamination chamber or region 24) to vaporizer 32. A blower 82, driven by a motor 84, is disposed within return conduit 46 between isolator or room 22 and vaporizer 32. Blower 82 is operable to circulate sterilant and a carrier gas, preferably air, through the closed loop system. A first filter 92 and catalytic destroyer 94 are disposed in return conduit 46 between blower 82 and isolator or room 22, as illustrated in FIG. 1. First filter 92 is preferably a HEPA filter and is provided to remove contaminants flowing through system 10. Catalytic destroyer 94 is operable to destroy vaporized hydrogen peroxide ($H_2O_2$) flowing therethrough, as is conventionally known. Catalytic destroyer 94 converts the vaporized hydrogen peroxide ($H_2O_2$) into water and oxygen. An air dryer 112, filter 114 and heater 116 are disposed within return line 46 between blower 82 and vaporizer 32. Air dryer 112 is operable to remove moisture from air blown through the closed loop system. Second filter 114 is operable to filter the air blown through return conduit 46 by blower 82. Heater 116 is operable to heat air blown through return conduit 46 by blower 82. In this respect, air is heated prior to the air entering vaporizer 32.

Figure 2:
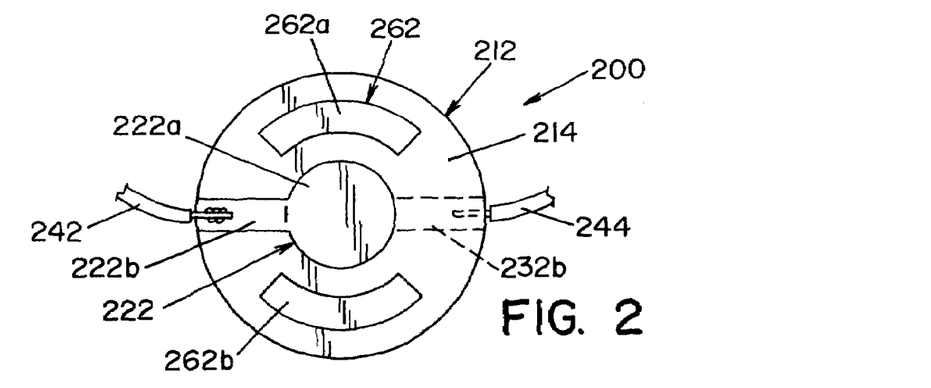
FIG. 2 is a top, plan view of a sensor for determining the concentration of an anti-microbial component used in a decontamination system.
Figure 3:
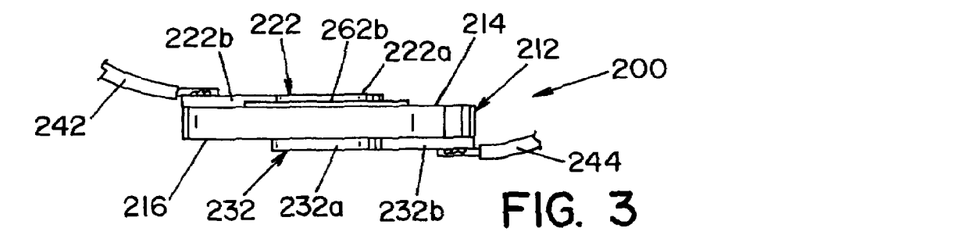
FIG. 3 is a side, elevation view of the sensor shown in FIG. 2.
Figure 4:
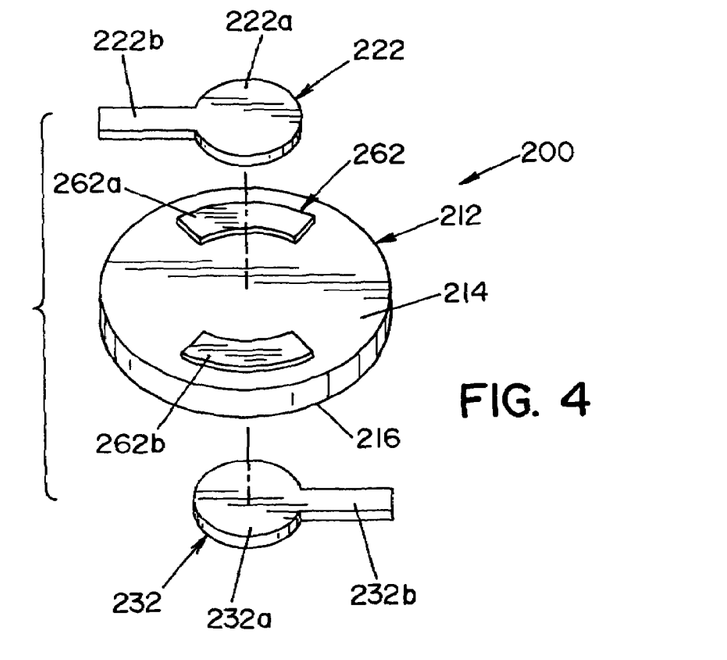
FIG. 4 is an exploded view of the sensor shown in FIG. 2.

A sensor 200 is disposed within chamber or room 24 to sense and/or monitor the concentration of hydrogen peroxide therein. Sensor 200 is best seen in FIGS. 2-4. Broadly stated, sensor 200 is comprised of an element 212 having a layer or coating 262 of a material that interacts with, or is reactive with, the sterilant or decontaminant used in system 10, such that mechanical motion or movement of element 212 is converted into an electrical signal.

Element 212 may be a moving or suspended component, but in a preferred embodiment, element 212 is a piezoelectric device, and more preferably, is a quartz crystal. Other piezoelectric materials, such as by way of example and not limitation, Rochelle salt, barium titanate, tourmaline, polyvinylidene fluoride and crystals that lack a center of symmetry are also contemplated. In the embodiment shown, element 212 is a flat, circular quartz disk having a first planar, major surface 214 and a second planar, major surface 216. An electrode 222 is disposed on the first major surface 214 and an electrode 232 is disposed optionally on the second major surface 216.

Electrode 222 includes a main body portion 222a that is centrally disposed on first major surface 214 and a leg portion 222b that extends in a first direction to the edge of element 212. Similarly, electrode 232 includes a main body portion 232a that is centrally disposed on second major planar surface 216, and a leg portion 232b that extends in a direction opposite to the first direction of leg portion 222b, wherein leg portion 232b extends to the edge of element 212. Main body portions 222a, 232a of electrodes 222, 232 are disposed respectively on first and second major surfaces 214, 216 to be aligned with each other on opposite sides of element 212. Leg portions 222b, 232b extend in opposite directions from central body portions 222a, 232a, as best seen in the drawings. Electrodes 222, 232 are deposited onto first and second planar surfaces 214, 216. Electrodes 222, 232 may be formed of any electrically conductive material, but are preferably formed of copper, silver or gold. Electrical leads 242, 244 are attached to leg portions 222b, 232b of electrodes 222, 232. Leads 242, 244 are soldered, braised or welded to electrodes 222, 232 to be in electrical contact therewith.

At least one of the two major surfaces 214, 216 of element 212 is coated with a layer 262 of a material that interacts, or is reactive with, the sterilant to be used within system 10. In the embodiment shown, layer 262 is on major surface 214. In the embodiment shown, layer 262 is defined by two arcuate or crescent-shaped layer areas 262a, 262b of material applied to first major surface 214 of element 212. Arcuate layer areas 262a, 262b are disposed on first major surface 214 such that electrode 222 is disposed therebetween. The material forming layer areas 262a, 262b are preferably fixedly attached to surface 214 of element 212. As will be appreciated from a further description of the present invention, the mass of the material on element 212 is dependent upon the desired performance characteristics of sensor 200. As indicated above, the material forming layer areas 262a, 262b are preferably one that interacts or reacts with the sterilant or decontaminant used within system 10.

In a preferred embodiment of the present invention, the sterilant to be detected is vaporized hydrogen peroxide (VHP), and the material that forms layer areas 262a, 262b on first major surface 214 of sensor 200 is a metal oxide, namely, lead dioxide ($PbO_2$). It is believed that other metal oxides having various states, such as silver (II) oxide (AgO) or manganese (IV) oxide ($MnO_2$), may be used. It is also contemplated that metal oxides having mixed valency states, such as by way of example and not limitation, a metal oxide having a mixture of single and divalent oxide states may be used.

Layer areas 262a, 262b are preferably formed by a thin film deposition process. It should be understood that the term "thin film deposition" is inclusive of Physical Vapor Deposition (PVD) and Chemical Vapor Deposition (CVD). PVD is used in accordance with a preferred embodiment of the present invention. PVD includes the processes of evaporation, ion-beam assisted electron beam deposition, and "sputtering" (which includes ion beam deposition).

Evaporation includes processes such as electron beam evaporation (also referred to herein as "electron beam deposition"), as well as processes wherein a material is heated inside a vacuum chamber by a heater to form a vapor, without use of an electron beam. The heating is classified as (a) resistive or (b) inductive. The evaporation processes which do not use an electron beam are commonly used to deposit $SiO_2$ or SiO thin films, and can also be used in conjunction with an ion-beam assist. Ion-beam assisted evaporation (with and without use of an e-beam) are collectively referred to herein as "ion-bean assisted deposition."

Sputtering refers to a glow discharge process whereby bombardment of a cathode releases atoms from the surface which then deposit onto a nearby surface to form a coating. For example, sputtering occurs when energetic ionized particles impinge on the surface of a target material, causing the emission of particles and erosion of the surface of a solid. This particular sputtering process is also referred to herein as "ion beam deposition."

Sensor 200 is disposed within chamber or region 24, and is connected to a system controller 132, that is schematically illustrated in FIG. 1, to provide electrical signals thereto. Controller 132 is a system microprocessor or microcontroller programmed to control the operation of system 10. As illustrated in FIG. 1, controller 132 is also connected to motors 64, 84, pressure switch 72 and balance device 56. Controller 132 includes an oscillating circuit (not shown) that is connected to sensor 200 to convert movement of sensor 200 into electrical signals, as is conventionally known. Controller 132 also includes stored data indicative of the electrical responses of sensor 200 to predetermined concentrations of a sterilant to be sensed. In the embodiment heretofore described, where element 212 is a quartz crystal and layer areas 262a, 262b are lead dioxide, the data relating to sensor 200 that is stored within controller 132 is empirical data accumulated under controlled, laboratory conditions.

In accordance with the present invention, the empirical data relating to sensor 200 that is stored in controller 132 may be acquired as follows. The natural frequency of a quartz crystal (without a coating thereon) is measured. The lead dioxide is applied to the quartz crystal and the mass of the coating is determined using the Sauerbre equation. The quartz crystal is then exposed to various, controlled concentrations of vaporized hydrogen peroxide (VHP). A graph of the change in frequency per unit mass of coating (or, using the Sauerbre equation, the change in weight per unit mass of coating) versus concentration of sterilant or oxidant is produced and stored in a data storage device within controller 132. Alternatively, the data could be stored not as a graph but rather in look up tables. As will be appreciated, if a coating of uniform thickness is applied to a crystal, the change in frequency or weight could be normalized on a per unit surface area basis.

As suggested, in one embodiment, the change in frequency or weight is divided by the mass of the coating applied to the quartz crystal so that regardless of the mass of coatings applied to other crystals, the change in frequency will be normalized to a unit mass of the coating. Data taken with other quartz crystals that may have coatings of different amounts Of mass than the laboratory crystal can still be compared to the stored data obtained from the laboratory crystal as both sets of data will be normalized to a change in frequency or weight per unit mass of the coating. It will be appreciated that with modern deposition means, it may not be necessary to normalize the data as coatings with little physical variation can be deposited from one crystal to the next.

In another embodiment, a quartz crystal is coated with lead oxide and is then exposed to known concentrations of vaporized hydrogen peroxide so as to develop a set of data, or a curve, of equilibrium frequency reduction values as a function of concentration of vaporized hydrogen peroxide for the quartz crystal. The coated quartz crystal is then installed in a system 10. The associated set of data, or curve, is programmed or stored in controller 132 of the system 10. Thus, the data stored in the system 10 matches the crystal sensor within the system 10, thereby providing a standardized system. In this maimer, each system 10 has a coated quartz crystal sensor with an associated standardized data set therein, as the stored data set was produced by exposing that specific quartz crystal to known concentrations of vaporized hydrogen peroxide.

The present invention shall now be further described with reference to the operation of system 10. Sensor 200 operates based upon the concept that the frequency of a piezoelectric device will change in relation to a change in mass of a layer on the device, as a result of exposure to vaporized hydrogen peroxide.

Specifically, the frequency of a piezoelectric device is related to the mass change, as determined by the Sauerbre equation:

$$\Delta f = -(C_f)(\Delta m)$$

$$\Delta f = -(f_o^2/N\rho)\Delta m$$

where:
$\Delta f$ is the frequency change
$\Delta m$ is the mass change per unit area on the surface of the piezoelectric device
$C_f$ is a sensitivity constant
$f_o$ is the operating frequency of the piezoelectric device prior to the mass change
N is the frequency constant for the piezoelectric device
$\rho$ is the density of the piezoelectric device A typical sterilization/decontamination cycle includes a drying phase, a conditioning phase, a decontamination phase and an aeration phase. In a preferred embodiment, a sterilant solution of 30% by weight hydrogen peroxide and 70% by weight water is used. However, other concentrations of hydrogen peroxide and water are contemplated.

Isolator or room 22, supply conduit 42 and return conduit 46 define a closed loop conduit circuit. When a sterilization/decontamination cycle is first initiated, controller 132 causes blower motor 84 to drive blower 82, thereby causing a carrier gas to circulate through the closed loop circuit. In the embodiment shown, the carrier gas is air. During a drying phase, vaporizer 32 is not operating. Air dryer 112 removes moisture from the air circulating through the closed loop system, i.e., through supply conduit 42, return conduit 46 and sterilization/decontamination chamber or region 24 or isolator or room 22, as illustrated by the arrows in FIG. 1. When the air has been dried to a sufficiently low humidity level, the drying phase is complete.

The conditioning phase is then initiated by activating vaporizer 32 and sterilant supply motor 64 to provide sterilant to vaporizer 32. As noted above, a preferred sterilant is a hydrogen peroxide solution comprised of about 35% hydrogen peroxide and about 65% water. Sterilant solutions comprised of different ratios of hydrogen peroxide are also contemplated. Within vaporizer 32, the liquid sterilant is vaporized to produce vaporized hydrogen peroxide (VHP) and water vapor, in a conventionally known manner. The vaporized sterilant is introduced into the closed loop conduit circuit and is conveyed through supply conduit 42 by the carrier gas (air) into sterilization/decontamination chamber or region 24 within isolator or room 22. During the conditioning phase, VHP is injected into sterilization/decontamination chamber or region 24 at a relatively high rate to bring the hydrogen peroxide level up to a desired level in a short period of time. During the conditioning phase, blower 82 causes air to continuously circulate through the closed loop system. As VHP enters chamber or region 24 from vaporizer 32, VHP is also being drawn out of chamber or region 24 through catalytic destroyer 94 where it is broken down into water and oxygen.

After the conditioning phase is completed, the decontamination phase is initiated. During the decontamination phase, the sterilant injection rate to vaporizer 32 and to sterilization/decontamination chamber or region 24 is decreased to maintain the hydrogen peroxide concentration constant at a desired level. The decontamination phase is run for a predetermined period of time, preferably with the hydrogen peroxide concentration remaining constant at a desired level, for a predetermined period of time that is sufficient to effect the desired sterilization or decontamination of sterilization/decontamination chamber or region 24, and items therein.

After the decontamination phase is completed, controller 132 causes vaporizer 32 to shut down, thereby shutting off the flow of vaporized hydrogen peroxide (VHP) into sterilization/decontamination chamber or region 24.

Thereafter, the aeration phase is run to bring the hydrogen peroxide level down to an allowable threshold (about 1 ppm). In this respect, as will be appreciated, blower 82 continues to circulate the air and sterilant through the closed loop system, thereby causing the last of the vaporized hydrogen peroxide (VHP) to be broken down by catalytic destroyer 94.

As illustrated in FIG. 1, sensor 200 is exposed to the atmosphere within region or chamber 24. During the aeration phase of system 10, an operating frequency $f_o$ of sensor 200 is determined by controller 132. Operating frequency $f_o$ is essentially a baseline frequency of sensor 200 prior to any mass change that would be the result of exposure of sensor 200 to the vaporized hydrogen peroxide. During the conditioning phase, sensor 200 is exposed to the vaporized hydrogen peroxide entering chamber or region 24. The hydrogen peroxide ($H_2O_2$) produces a reaction with the lead dioxide ($PbO_2$). It is believed that the following reaction occurs:

$$PbO_2 + H_2O_2 \leftrightarrow PbO_2 + H_2O + (\frac{1}{2})O_2$$

The reaction between the lead dioxide ($PbO_2$) of layer areas 262a, 262b and the hydrogen peroxide ($H_2O_2$) produces a change in the mass of layer areas 262a, 262b. The change in mass of sensor 200 results in a change in the operating frequency $f_o$ thereof. Controller 132 monitors the frequency to determine "measured frequencies" $f_m$ during the conditioning phase, during the decontamination phase and during the aeration phase. The measured frequencies $f_m$ are compared to the baseline operating frequency $f_o$ to determine a change in frequency. Controller 132 then determines the concentration of vaporized hydrogen peroxide (VHP) with space of region 24 at a given point in time by comparing the change in frequency at that given point in time with corresponding data stored in controller 132. Controller 132 is thus able to determine the concentration of hydrogen peroxide ($H_2O_2$) within region or chamber 24 at a given point in time. In this respect, it is believed that a change in frequency of sensor 200 is directly proportional to a change in concentration of hydrogen peroxide. Thus, the concentration of hydrogen peroxide within chamber or region 24 can be sensed at a specific point in time, and continuously monitored, based upon a change in frequency of sensor 200.

The present invention shall now be further described with respect to an Example wherein a quartz crystal is coated with lead dioxide ($PbO_2$) and exposed to vaporized hydrogen peroxide (VHP).

EXAMPLE

A 10 MHz quartz crystal is coated with lead dioxide (99.99% $PbO_2$) through a vapor deposition process (thermal evaporation at $10^{-7}$ torr). The weight of the quartz crystal is increased by about $10^{-3}$ g after a thermal evaporation process of 1.5 g of lead dioxide ($PbO_2$). The nominal area of the lead dioxide ($PbO_2$) coating on the crystal is about 93.1 $mm^2$. The sensor is placed in the path of a carrier gas moving at a set flow rate along the path. The carrier gas is dry air that is heated to about 30° F. Once the vibration frequency of the sensor is stabilized, a known concentration of vaporized hydrogen peroxide (VHP) is introduced into the carrier gas (air). The change of frequency with respect to time is measured. Once an equilibrium is reached, the supply of vaporized hydrogen peroxide (VHP) to the carrier gas is terminated. The change of frequency with respect to time is measured until another stable vibrational condition is established.

Figure 5:
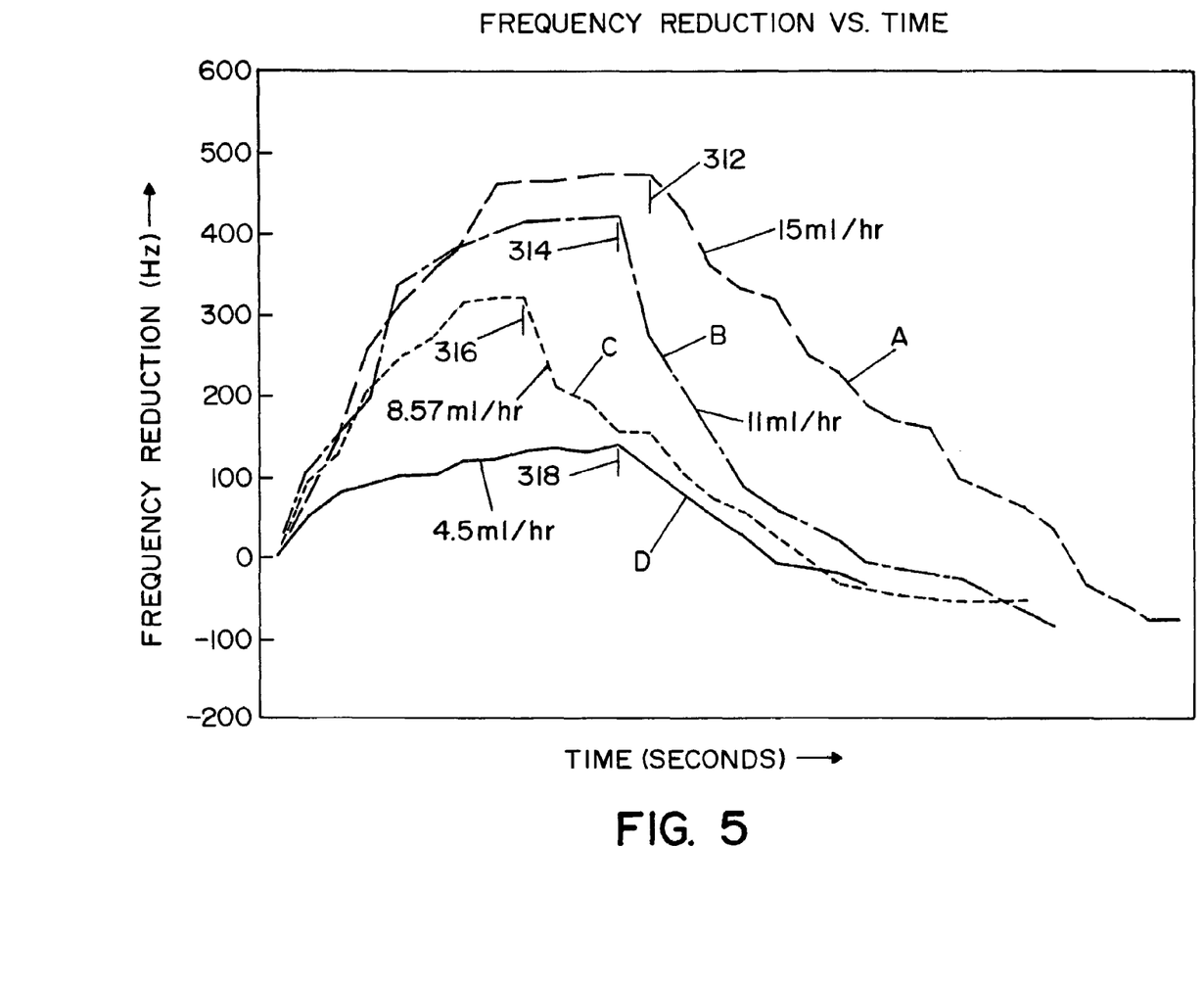
FIG. 5 is a graph showing the frequency response of a sensor according to the present invention over time from an initial condition wherein the sensor is not exposed to vaporized hydrogen peroxide (VHP) to a condition wherein the sensor is exposed to different concentrations of vaporized hydrogen peroxide (VHP)

The same test is performed for different concentrations of vaporized hydrogen peroxide (VHP). It is found that in each concentration of vaporized hydrogen peroxide (VHP), the equilibrium frequency of the sensor is established in about 7 to 8 minutes. A linear relationship between the equilibrium frequency change and the concentration of vaporized hydrogen peroxide (VHP) is found. FIG. 5 is a graph showing the change in frequency as a function of time for four (4) different vaporized hydrogen peroxide (VHP) concentration levels. In FIG. 5, the change in frequency over time is shown. In this respect, line A shows the reduction in frequency to a peak value over time for a vaporized hydrogen peroxide (VHP) flow rate of 15 milliliter per hour. Line B shows the frequency reduction to a peak value over time for a vaporized hydrogen peroxide (VHP) flow rate of 11 milliliter per hour. Line C shows the frequency reduction to a peak value over time for a vaporized hydrogen peroxide (VHP) flow rate of 8.57 milliliters per hour, and line D shows the frequency reduction to a peak value over time for a vaporized hydrogen peroxide (VHP) flow rate of 4.5 milliliters per hour.

Location 312 along line A indicates when the flow of vaporized hydrogen peroxide (VHP) to the carrier gas is terminated. Location 314 along line B indicates when the flow of vaporized hydrogen peroxide (VHP) to the carrier gas is terminated. Location 316 along line C indicates when the flow of vaporized hydrogen peroxide (VHP) to the carrier gas is terminated. Location 318 along line D indicates when the flow of vaporized hydrogen peroxide (VHP) to the carrier gas is terminated. As shown in FIG. 5, for each test, the frequency of sensor 200 begins to increase when the vaporized hydrogen peroxide (VHP) flow to the carrier gas is terminated. That is, when the source of vaporized hydrogen peroxide (VHP) is terminated, the reduction in frequency peaked, and thereafter, the frequency of sensor 200 increases, i.e., the reduction in frequency begins to decline. This graph illustrates the reusable nature of crystals coated with lead dioxide ($PbO_2$) as a hydrogen peroxide sensor.

Figure 6:
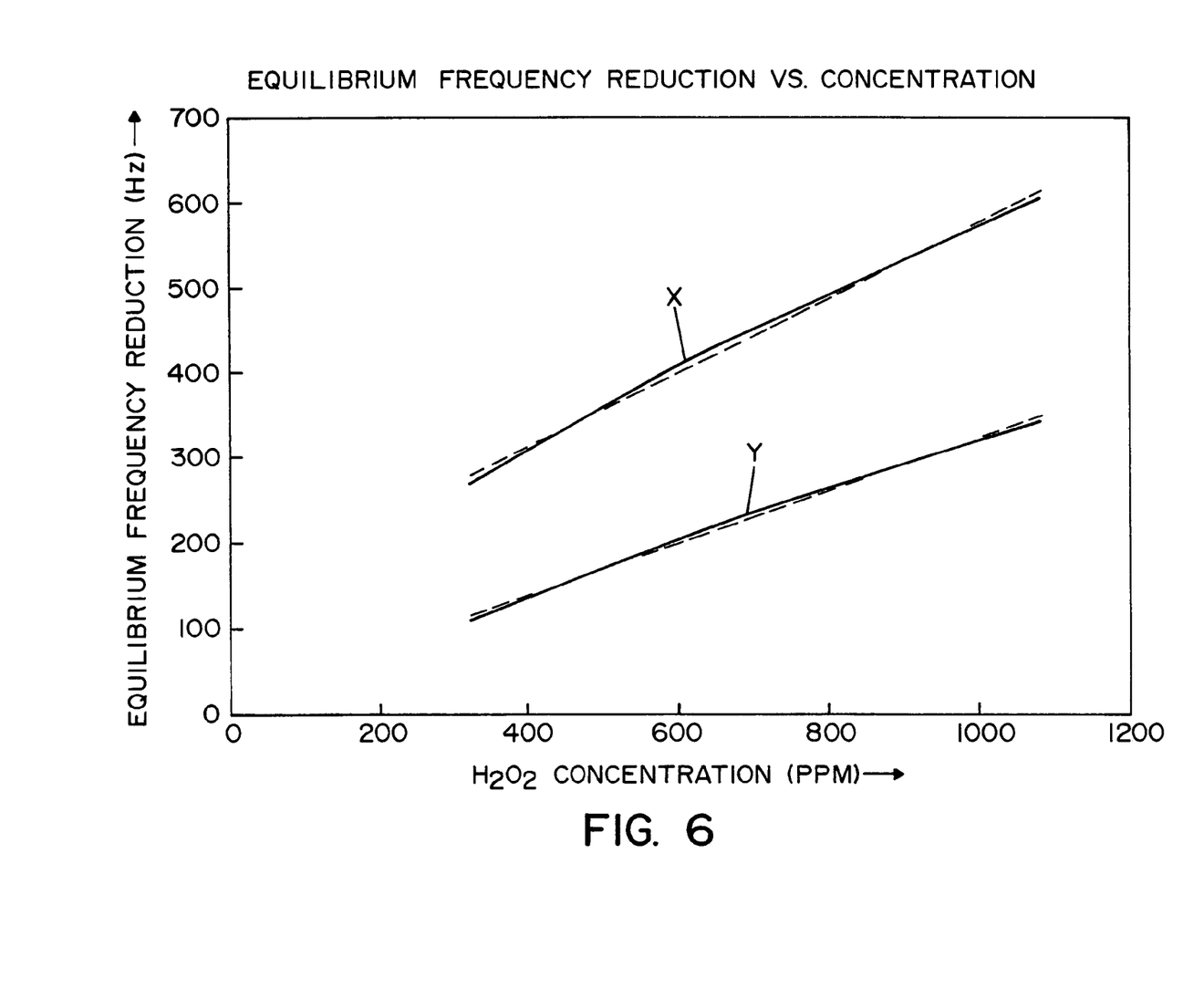
FIG. 6 is a graph showing the equilibrium frequency reduction versus sterilant concentration for a sensor according to the present invention.

FIG. 6 is a graph showing the results of two tests correlating equilibrium frequency reduction to the concentration of vaporized hydrogen peroxide (VHP) in a region. Curves X and Y (shown in solid lining) show measured test results, and the dashed lines associated with curves X and Y show the best straight line fit for each curve. Curves X and Y show a fairly linear relationship between the equilibrium frequency reduction and the concentration of vaporized hydrogen peroxide (VHP) in parts per million.

The foregoing results show that a quartz crystal coated with lead dioxide ($PbO_2$) is responsive to the presence of vaporized hydrogen peroxide (VHP). The test results further suggest that the reaction is catalytic, indicating that sensor 200 returns to its original state following the removal of vaporized hydrogen peroxide (VHP) from the vicinity of sensor 200. No significant change, beyond background noise, is found when sensor 200 is exposed to water vapor alone. Sensor 200 is thus suitable for repeated use in detecting the presence of vaporized hydrogen peroxide (VHP). It is believed that the sensitivity of sensor 200, as heretofore described, can be varied by varying the amount, i.e., the mass, of the material deposited onto the quartz crystal.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

It should be appreciated that while a preferred embodiment of the present invention has been described with reference to sensing a concentration of vaporized hydrogen peroxide, it is contemplated that the present invention finds utility in sensing a concentration of other chemical components. These chemical components may comprise deactivating chemicals, including, but not limited to, chemicals selected from the group consisting of: hypochlorites, iodophors, quaternary ammonium chlorides (Quats), acid sanitizers, aldehydes (formaldehyde and glutaraldehyde), alcohols, phenolics, peracetic acid (PAA), and chlorine dioxide.

Specific examples of deactivating chemicals, include, but are not limited to, liquid hydrogen peroxide, peracids such as peracetic acid, bleach, ammonia, ethylene oxide, fluorine containing chemicals, chlorine containing chemicals, bromine containing chemicals, vaporized hydrogen peroxide, vaporized bleach, vaporized peracid, vaporized peracetic acid, ozone, ethylene oxide, chlorine dioxide, halogen containing compounds, other highly oxidative chemicals (i.e., oxidants), and mixtures thereof.

As indicated above, the chemical components introduced into chamber or region 24 may also include base chemicals. Examples of base chemicals, include, but are not limited to, water, de-ionized water, distilled water, an alcohol (e.g., a tertiary alcohol), a glycol-containing chemical compound, and mixtures thereof. Glycol-containing chemical compounds include, but are not limited to, polyethylene glycol, diethylene glycol, triethylene glycol, tetraethylene glycol, glycol ethers, polypropylene glycol, propylene glycol, de-ionized water vapor, distilled water vapor, a vaporized alcohol (e.g., a tertiary alcohol), and mixtures thereof. As indicated above, the base chemical may itself be a deactivating chemical. Therefore, the base chemical may also be any one of the deactivating chemicals listed above.

Some typical combinations of a deactivating chemical and a base chemical, include, but are not limited to, hydrogen peroxide and water, bleach and water, peracid and water, peracetic acid and water, alcohol and water, and ozone dissolved in a glycol, an alcohol (e.g., tertiary alcohol), or water. Some examples of gaseous atmospheres that may be created inside chamber or region 24, include, but are not limited to: ozone; vaporized hydrogen peroxide and water vapor; ethylene oxide; vaporized hydrogen peroxide, water vapor and ozone; vaporized hydrogen peroxide, water vapor and ethylene oxide; ozone and ethylene oxide; and vaporized hydrogen peroxide, water vapor, ozone and ethylene oxide.

The use of other electrical/mechanical devices that support a material sensitive to vaporized hydrogen peroxide (VHP) as discussed herein are also contemplated. In such a case, a change in the physical properties of the electrical/mechanical device as it is exposed to vaporized hydrogen peroxide (VHP) is correlated to a change in the concentration of the vaporized hydrogen peroxide (VHP).

Other modifications and alterations will occur to others upon their reading and understanding of the specification. It is intended that all such modifications and alterations be included insofar as they come within the scope of the invention as claimed or the equivalents thereof.

Having described the invention, the following is claimed:

1. A method of determining the presence of a sterilant in a region of a decontamination system having a chamber defining the region and a circulation system for supplying the sterilant to the region, comprising the steps of:
   providing in said region an element having piezoelectric properties with a metal oxide coating having a tetravalent state;
   determining a baseline frequency of oscillation for said element in the absence of the sterilant;
   determining a sensed frequency of oscillation for said element when exposed to the sterilant in said region; and
   determining the concentration of the sterilant in said region based upon the difference between said sensed frequency and said baseline frequency, wherein said sterilant includes hydrogen peroxide and wherein said metal oxide is lead dioxide.

2. A method as defined in claim 1, wherein said hydrogen peroxide is vaporized.

3. A method as defined in claim 1, wherein said sterilant includes water vapor.

4. A method as defined in claim 1, wherein said element is a crystal that lacks a center of symmetry.

5. A method as defined in claim 4, wherein said crystal is a quartz crystal.

6. A method as defined in claim 5 having a resonant frequency of 5 MHz or 10 MHz.

7. A system for the deactivation of bio-contamination, comprising:
   a system for moving a sterilant through a space;
   a piezoelectric device that supports a metal oxide in a tetravalent state that interacts with said sterilant, said piezoelectric device having a frequency that changes in response to the presence of said sterilant; and
   a controller having data stored therein relating to said piezoelectric device, said data relating a frequency of said piezoelectric device to a concentration of said sterilant, wherein said metal oxide is lead dioxide.

* * * * *